United States Patent [19]
Travis

[11] Patent Number: 5,111,806
[45] Date of Patent: May 12, 1992

[54] SUPPORT BELT WITH COLOR INDICATOR

[75] Inventor: Jack M. Travis, Wake Forest, N.C.

[73] Assignee: Champion Ergonomics, Inc., Wake Forest, N.C.

[21] Appl. No.: 739,301

[22] Filed: Aug. 1, 1991

[51] Int. Cl.$^5$ ............................ A61F 5/02; A61F 5/37
[52] U.S. Cl. ....................................... 602/19; 128/876
[58] Field of Search ............... 128/78, 75, 95.1, 96.1, 128/100.1, 101.1, 876, 87 R; 2/318

[56] References Cited

U.S. PATENT DOCUMENTS

| | | | |
|---|---|---|---|
| 2,104,699 | 1/1938 | O'Dell | 128/78 |
| 2,117,309 | 5/1938 | Fritsch | 128/78 |
| 2,723,664 | 11/1955 | Davis | 128/78 |
| 3,441,027 | 4/1969 | Lehman | 128/78 |
| 3,561,434 | 2/1971 | Kilbey | 128/78 |
| 3,568,670 | 3/1971 | Gaylord | 128/78 |
| 3,570,480 | 3/1971 | Stubbs | 128/78 |
| 3,920,008 | 11/1975 | Lehman | 128/96.1 |
| 4,099,524 | 7/1978 | Cueman | 128/78 |
| 4,884,562 | 12/1989 | Stone | 128/78 |
| 4,960,112 | 10/1990 | Anderegg | 128/78 |

Primary Examiner—Robert A. Hafer
Assistant Examiner—Michael Brown
Attorney, Agent, or Firm—Rhodes, Coats & Bennett

[57] ABSTRACT

A support belt for labores provides increased support for abdominal muscles and back muscles in the lumbar region, particularly for those engaged in work involving lifting. The support belt includes a primary band adapted to extend around the user's waist and a secondary band. The secondary band is made of an elastic material and is adapted to stretch in a longitudinal direction to extend around the user's waist. The ends of the secondary band can be overlapped and secured to one another when the secondary band is in a stretched condition. By stretching the secondary band, the tension forces in the secondary band provide support for the wearer's back and abdominal muscles and helps avoid excessive curvature of the spine during lifting. To assure that the proper support is provided, the secondary band includes color indicating means for indicating when the proper amount of tension is applied to the secondary band. First and second fastening components are attached to the free ends of the secondary band which are overlapped with one another. The fastening component on the underlying band portion is made of a color which contrasts sharply with the band material so that any portion of the fastening component exposed when the belt is worn will be clearly visible. The fastening components are arranged such that the appropriate degree of tension in the secondary band is provided when the fastening component on the underlying band means is completely covered. Accordingly, any portion of the fastening component which is exposed while the belt is being worn will be clearly visible and will indicate that the band is not being properly worn.

9 Claims, 5 Drawing Sheets

SUPPORT BELT WITH COLOR INDICATOR

FIELD OF THE INVENTION

The present invention relates to back supports and more particularly to back supports belts adapted to provide increased support for abdominal muscles and back muscles in the lumbar region.

BACKGROUND OF THE INVENTION

Back supports are widely used to avoid injury by workers whose tasks involve heavy lifting. Employers often require their employees to wear such back supports in order to reduce their own liability and to avoid the expense and waste resulting from worker disability. When used properly, back supports are very effective in preventing back injury, particularly injuries resulting from excessive lordosis, or forward curvature of the spine. However, when used improperly, whether inadvertently or deliberately, the effectiveness of a back support is reduced or eliminated.

A commonly used back support belt includes a relatively wide primary belt having one or more rigid lumbar supports and a secondary band. The back provides increased support for back and abdominal muscles, and helps prevent excessive curvature of the spine. The belt often has VELCRO fasterners as a coupling and adjustment means. It may also be provided with shoulder straps attached to the belt to keep the support from slipping downwardly where it is less effective. One such belt is described in U.S. Pat. No. 3,920,008 issued on Nov. 18, 1975 to Lehman.

It is very important to the effectiveness of the back support belt that it be worn in the proper location and that the tension of the belt be properly adjusted to provide adequate support for the abdominal and back muscles. If the support is not properly adjusted, it is less effective or completely ineffective in protecting the wearer from injury. If the employer has provided his/her employees with a back support belt and it is not worn properly, then he receives none of the benefits associated with the belt, such as decreased injury related losses. For this reason, employers have an interest in insuring that the back support belts are properly worn by their employees.

Most workers which are required to wear back support belts lack training in the proper use of the belt, or purposefully misuse the belt by wearing the belt loosely for comfort. Further, there is no convenient way for a supervisor to determine whether the employees under his or her direction are properly using the belt so as to obtain its full benefits. There is presently a need for both employees and supervisors to determine whether a back support belt is being worn with the proper tension or being worn loosely so as to be less than ideally effective.

SUMMARY AND OBJECTS OF THE INVENTION

The back support belt of the present invention is specifically designed to provide an easy and convenient method of determining when the belt is being properly worn. The back support belt of the present uses a colored fastening means in combination with specific design criteria to indicate when the belt is being properly worn, and when it is not being properly worn.

In a preferred embodiment of the invention, the support belt includes a primary band, and a secondary band, which provides the majority of the support for the user's abdominal and back muscles. The secondary band is made of an elastic material and is stretchable in the longitudinal direction so as to extend around the wearer's waist. When properly stretched, the ends of the secondary band overlap one another. A cooperative fastening means such as a hook and loop-type fastener, is used to secure the free ends of the secondary band means in an overlapping condition. The fastening component on the underlying free end is made of a color which starkly contrasts with the band material. Further, the length of the secondary band means and the placement of the fastening components on the band means is selected so that the proper band tension is provided when the colored fastening component is completely covered by the overlying free end of the secondary band means. If the belt is not being properly worn, such as being worn loosely, a portion of the colored fastening component will be exposed. Since the colored fastening component contrasts sharply with the band material, it will be clearly visible. The exposed colored fastening component will indicate to the employee, and to any supervisor overseeing him, that the belt is not properly fitted.

Accordingly, it is an object of the present invention to provide a support belt for use by workers involved in manual labor to help prevent back injury by providing increased support for abdominal muscles and muscles in the lumbar region of the back.

Another object of the present invention is to provide a work support belt to help prevent excessive curvature of the spine by increasing intra-abdominal pressure.

Another object of the present invention is to provide a work support belt that encourages proper posture during lifting and other manual labor by resisting excessive forward bending and other postures which contribute to back injury.

Another object of the present invention is to provide a work support belt which makes the user more aware of postures which contribute to back injury and helps train the user to avoid those postures.

Another object of the present invention is to provide a work support belt that helps reduce back injury by decreasing the pressure between the vertebrae in the lumbar region.

Another object of the present invention is to provide an easy and convenient method for employees and supervisors to determine when the work support belt is being properly worn so that all of the advantages and benefits of the work support belt can be realized.

It is an object of the present invention to provide a means for determining whether a back support belt is adjusted to the proper tension.

Other objects and advantages of the present invention will become apparent and obvious from a study of the following description and the accompanying drawings which are merely illustrative of such invention.

DETAILED DESCRIPTION OF THE INVENTION

Figure 1:
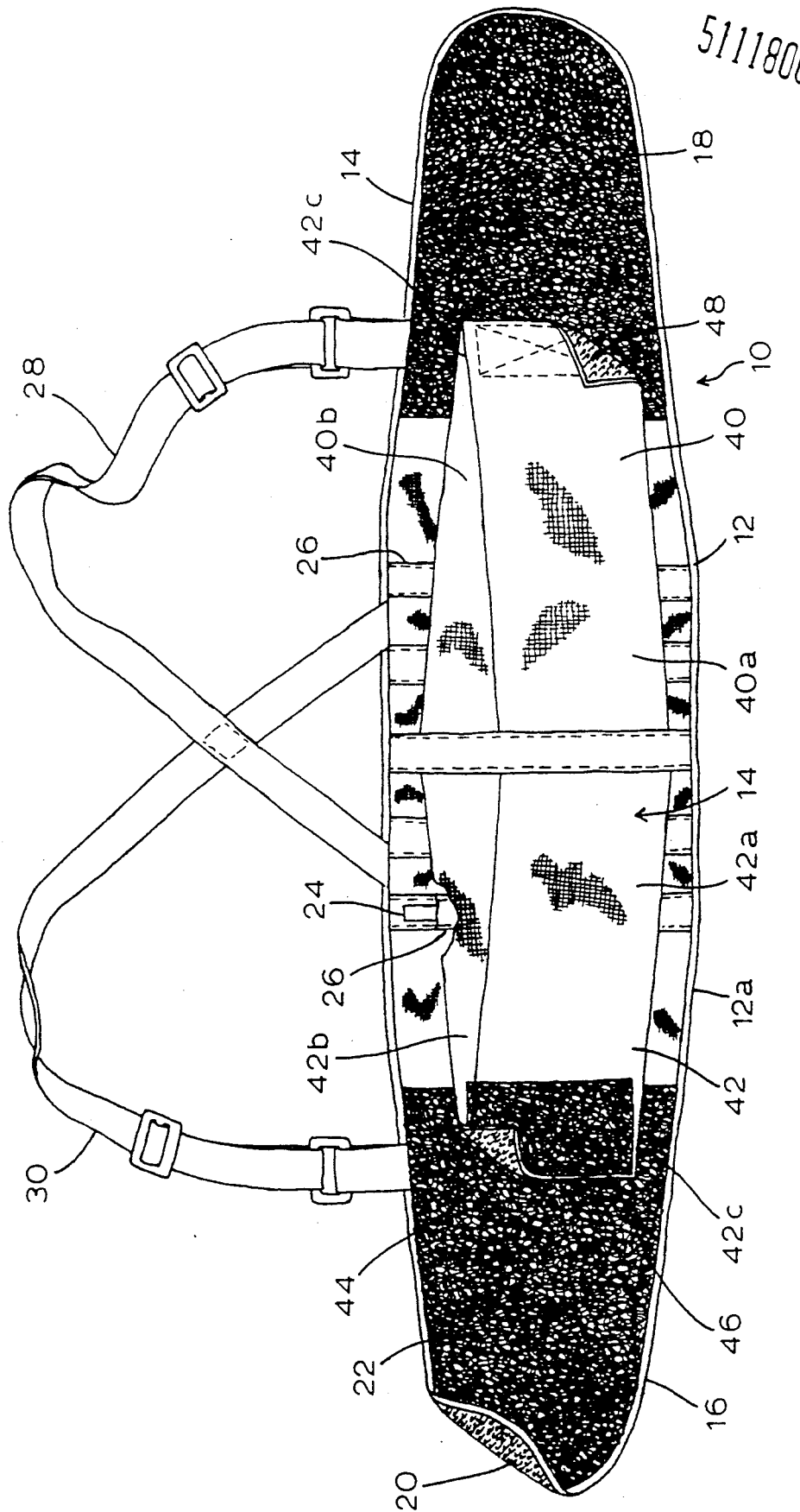
FIG. 1 is a plan view of the work support laid out flat.

Referring now to the drawings, and particularly to FIG. 1, the work support belt of the present invention is shown therein and indicated generally by the numeral 10. The belt 10 includes a primary support band 12 and a secondary tensioning band means 14.

The primary band 12 is constructed of spandex or other elastic material and includes an elastic banding material 12a extending around its periphery. The primary band includes two end portions 14 and 16. The primary band 12 has a length which is slightly less than the girth of the wearer. The band 12 is stretchable in the longitudinal direction to a length greater than the girth of the wearer so that the end portions 14 and 16 overlap.

Means are provided for securing the first and second end portions 14 and 16 in an overlapping condition. The fastening means comprises a hook and loop type fastener which is known commercially as "VELCRO." A pad of loop material 18 having a plurality of small loops is fastened to the outside of the first end portion 14, and a pad of hook material 20 having a plurality of small, relatively rigid hooks is fastened to the inside of the second end portion 16. When pressed together, the hooks on the hook pad 20 entangle with the loops on the loop pad 18, securing the two end portions 14 and 16 together. In the embodiment shown, the second end portion 16 also includes a pad of loop material 22 secured on the outside thereof for fastening the secondary band means 14 to the primary band 12 as will be hereinafter described.

The primary band 12 includes a back support means which comprises a plurality of vertical stays 24. For each vertical stay, an elongated strip 26 made of leather or other non-stretchable material is sewn onto to the primary band 12 in the area covering the lumbar region to form a pocket for the vertical stay 24. The vertical stays 24 are made of a relatively stiff, resilient material, such as spring steel, and extend vertically between the top and bottom edges of the primary band 12. The function of the vertical stays 24 is to resist curvature of the spine during lifting.

A pair of shoulder straps 28 and 30 are fixed at both ends to the primary band 12. The shoulder straps 28 and 30 each include a sliding buckle 32 for adjusting the length of the shoulder straps 28 and 30. Since the construction of shoulder straps are well-known to those skilled in the art, further discussion thereof is omitted.

In addition to the primary band 12, the present invention includes a secondary band means 14 for providing a lifting force on the wearer's abdominal and back muscles. The secondary band means comprises first and second band portions 40 and 42. Each band portion 40 and 42 is made of two strips of elastic band material 40a, 40b, and 42a, 42b, which are disposed at a slight angle relative to each other. The strips 40a, 40b and 42a, 42b are secured at one end to the center of the primary band 12. The opposite ends 40c and 42c are sewn together so that the individual strips act as a single piece of material.

The band portions 40 and 42 extend in opposite directions from the center of the primary band 12 where they are fixedly secure. The length of the band portions 40 and 42 is normally less than the girth of the wearer, but is stretchable in the longitudinal direction to extend the secondary band portions 40 and 42 around the wearer's waist and so that the ends 40c and 42c overlap. It will be appreciated, therefore, that the belt 10 must be made in various sizes to fit workers whose waist sizes vary.

At least one of the bands 40 and 42 is capable of being releasably secured to the primary band 12. In the embodiment shown, band portion 42 includes a pad of hook material 44 on the inside of the end 42c which meshes with the pad of loop material 22 on the outside of the end portion 16 forming a part of the primary band 12. A pad of loop material 46 is secured on the outside of the secondary band portion 42. This pad 46 is made of a colored material which contrasts sharply with the band material for reasons which will be hereinafter described. The opposite band portion 40 includes a pad of hook material 48 on the inside of the secondary band portion 40 which meshes with the pad 46 on the opposing band portion 42 to secure the ends 40c and 42c of the secondary band means 14 in an overlapping condition.

The work belt 10 of the present invention is particularly designed to apply pressure to the abdoment of the wearer. To assure that the proper amount of pressure is being applied, the present invention includes color indicating means for indicating when the secondary band means is tensioned sufficiently to provide adequate support. More particularly, the pad of loop material 46 which is fastened to the band portion 42 is made of a color which contrasts with the color of the band material. For example, the band material may be black while the pad 46 is bright red. The pad 46 must be positioned on the band portion 42 so that the pad 46 is completely covered by the band 40 when the ends are overlapped. If the secondary band is not stretched sufficiently to provide the necessary tension, a portion of the pad 46 will be exposed, and due to the contrasting colors, will be clearly visible.

Figure 2:
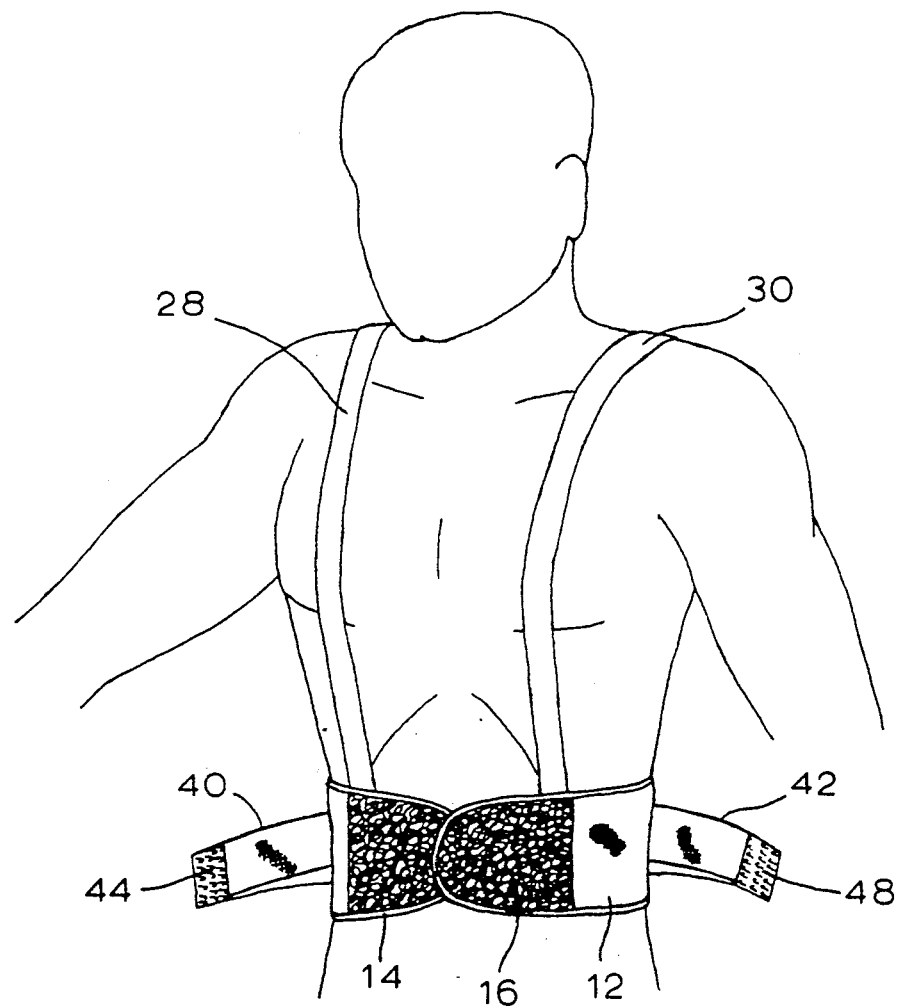
FIGS. 2-4 are perspective views illustrating how the belt is fitted around the wearer's waist.
Figure 3:
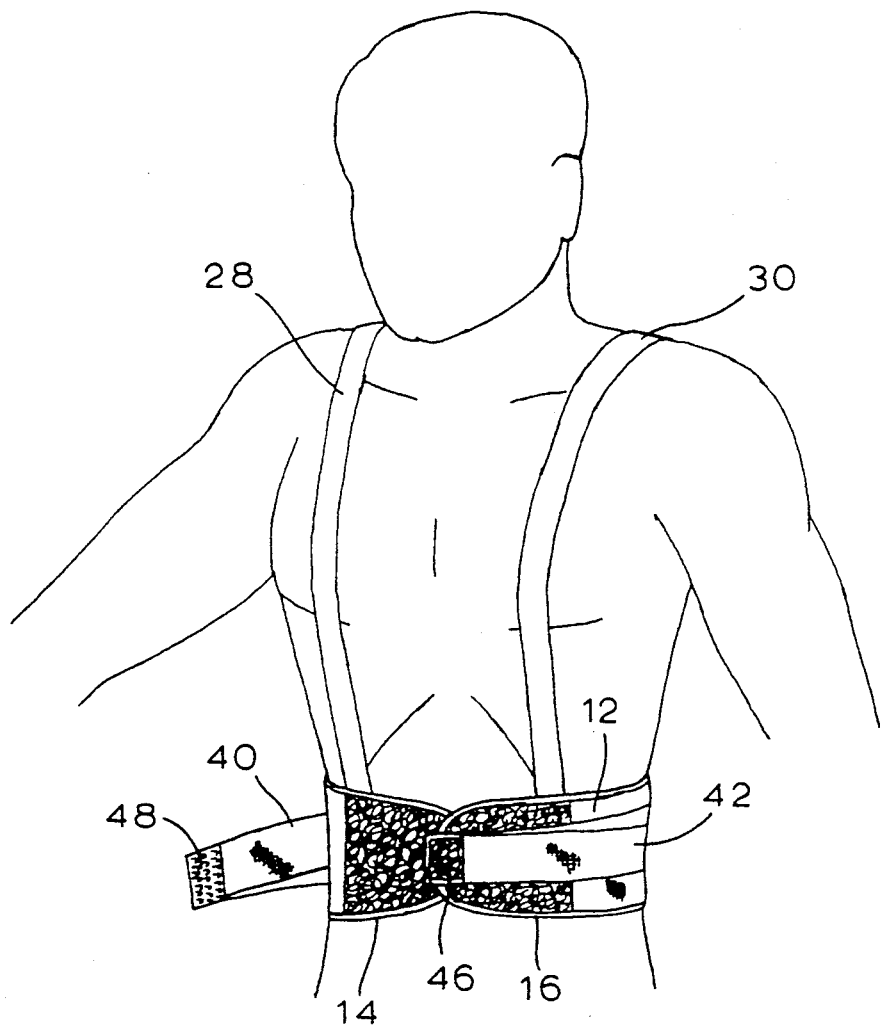
Figure 4:
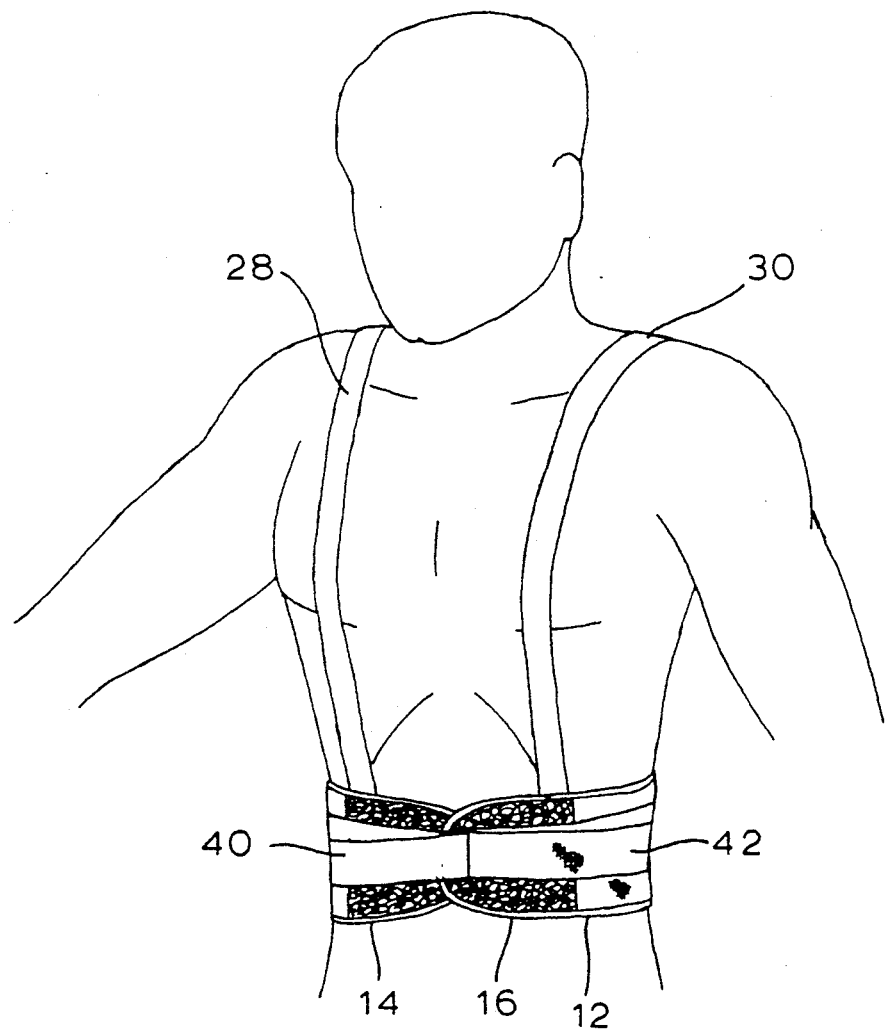

Referring now to FIGS. 2-4, the use of the work belt 10 of the present invention is illustrated. The user inserts his or her arms through the shoulder straps 28 and 30 and then stretches the primary band 12 until the end portions 14 and 16 of the primary belt 12 overlap one another. The end portions 14 and 16 are then secured together by pressing the hook pad 20 on the overlying end portion 16 against the loop pad 18 on the underlying end portion 14.

Figure 5:
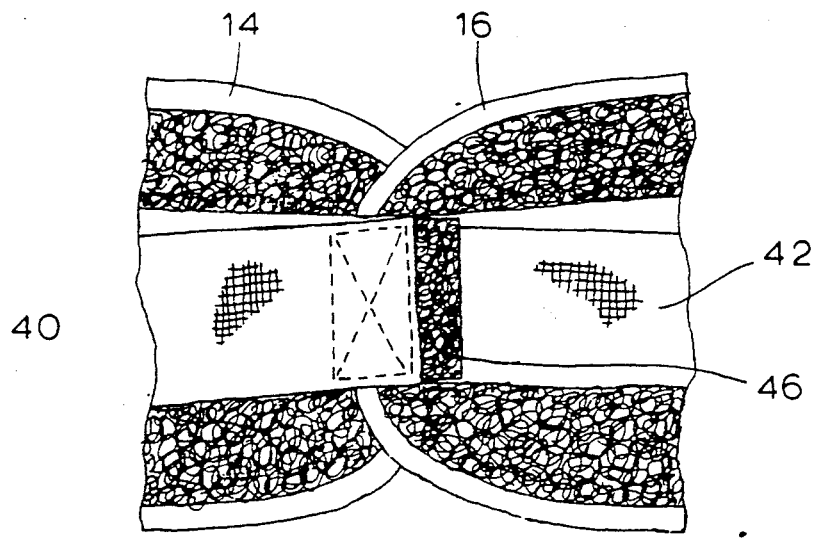
FIG. 5 is a partial front view of the work support belt when is not properly fitted.
Figure 6:
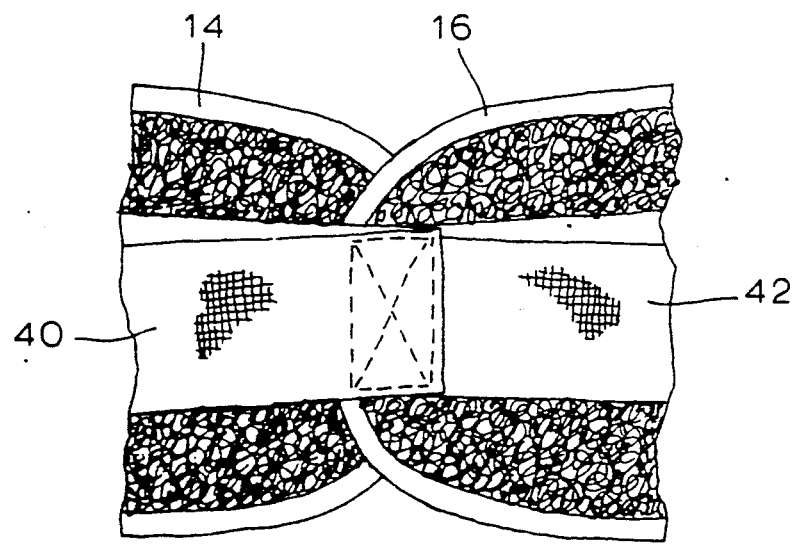
FIG. 6 is a partial front view of the work support belt when it is properly fitted.

Once the primary belt 12 is secured, band portion 42 of the secondary band means is stretched and secured to the end portion 16 of the primary band 12 as shown in FIG. 3. The opposite band portion 40 of the secondary band means 14 is then stretched and secured in overlapping fashion to the band portion 42 as shown in FIG. 4. The band portions 40 and 42 should be stretched sufficiently so that the pad 46 on band 42 is completely covered by the end of the band portion 40. FIG. 6 illustrates how the belt 10 appears when it is properly fitted. As shown in FIG. 6, the pad 46 is completely covered by the band portion 40. If any portion of the pad 46 is exposed, as shown in FIG. 5, this exposure will indicate that the belt 10 is not being properly worn and should be readjusted.

The work belt of the present invention is especially adapted to prevent injuries in many work situations, particularly while lifting heavy objects. The belt 10 helps support weak back and abdominal muscles which helps adnormal forward curvature of the spine in the lumbar region. When properly tensioned, the belt also increases intra-abdominal pressure which has been shown to give longitudinal support to the spine and help control excessive curvature of the lumbar spine.

Another advantage of the present invention is that it encourages proper posture during lifting by resisting forward bending which may increase lordosis. The increase pressure provided by the belt makes the user more aware of the outer limits of forward bending and trains the user to avoid those positions of posture which increase lordosis. The work belt of the present invention also reduces injury by decreasing the pressure between the vertebrae in the lumbar region.

The inherent advantages of the present invention will be realized, however, only when the belt is properly worn. Since most workers lack the knowledge and training to judge for themselves when the belt is properly fitted, the work belt 10 of the present invention provides a color indicator means to simplify the process for them. When the colored pad 46 is exposed, the belt is not being properly worn. When the colored pad is covered, this will indicate that the belt is fitted properly.

The present invention also provides a convenient method for plant managers and supervisors to oversee the use of the work belts. When a portion of the pad 46 is exposed, it will be clearly visible to the supervisor due to its contrasting color. The supervisor may then instruct the worker on how to properly fit the belt.

The present invention may, of course, be carried out in other specific ways than those herein set forth without departing from the spirit and essential characteristics of the invention. The present embodiments are, therefore, to be considered in all respects as illustrative and not restrictive and all changes coming within the meaning and equivalency range of the appended claims are intended to be embraced therein.

What is claimed is:

1. A back support belt sized to fit the waist of the user comprising:
   (a) a primary band having an intermediate portion, and two elastic end portions extending in opposite directions from the intermediate portion wherein said end portions overlap one another when said primary band is extended about the waist of the worker;
   (b) fastening means for fastening the end portions of the primary band in overlapping condition;
   (c) a secondary band for providing support for the user's abdominal and back muscles, said secondary band including first and second portions having one end fixed to the primary band and the opposite end being free, said secondary band portions being made of an elastic, which is stretchable in the longitudinal direction to extend around the user's waist;
   (d) cooperative fastening means for securing the free ends of the secondary band in an overlapping condition when the band is stretched; and
   (e) a tension indicator secured to the underlying free end portion of the secondary band for indicating when the secondary band is properly tensioned, said tension indicator being positioned on the underlying free end portion so as to be completely concealed when the first and second band portions are stretched sufficiently to provide the proper tension, and at least partially exposed when the first and second band portions are not stretched sufficiently to provide the proper tension.

2. The back support belt according to claim 1 wherein the primary band includes back support means for resisting excessive curvature of the spine.

3. The back support means according to claim 2 wherein the back support means comprises one or more vertical lumbar supports laterally spaced along the intermediate portion of the primary band.

4. The back support means according to claim 1 further including means for releasably securing the free ends of the secondary band portions to the primary band.

5. The back support belt of claim 1 wherein the tension indicator comprises a patch having a color which contrasts with the color of the secondary band means so that any exposed portion will be clearly visible.

6. A back support belt comprising:
   (a) an elastic band having two free ends which is stretched in normal use to extend around the wearer's midsection with the free ends overlapping one another to provide support for the wearer's back and abdominal muscles during manual labor; and
   (b) fastening means for securing the overlapping ends together; and
   (c) a tension indicator secured to the underlying free end of the elastic band for indicating when the elastic band is stretched sufficiently to provide the proper tension, said tension indicator being positioned on the underlying free end so as to be completely concealed when the elastic band is stretched sufficiently to provide the proper tension, and at least partially exposed when the elastic band is not stretched sufficiently to provide the proper tension.

7. The back support belt according to claim 6 wherein the elastic band includes back support means for resisting excessive curvature of the spine.

8. The back support means according to claim 6 wherein the back support means comprises one or more vertical lumbar supports laterally spaced along the intermediate portion of the primary band.

9. The back support belt of claim 6 wherein the tension indicator comprises a patch having a color which contrasts with the color of the elastic band means so as to be clearly visible when exposed.

* * * * *